(12) United States Patent
Brown et al.

(10) Patent No.: US 8,551,547 B2
(45) Date of Patent: Oct. 8, 2013

(54) PROCESS FOR THE PREPARATION OF ANGIOGENIN

(75) Inventors: Andrew Brown, Cobram (AU);
Michelle Rowney, Port Campbell (AU);
Peter Hobman, Melbourne (AU);
Matthew McDonagh, Williamstown (AU); Angus Tester, Moonee Ponds (AU); Benjamin Cocks, Viewbank (AU)

(73) Assignees: Murray Goulburn Co-operative Co., Limited, Brunswick, Victoria (AU);
Agriculture Victoria Services Pty Ltd., Atwood, Victoria (AU)

( * ) Notice: Subject to any disclaimer, the term of this patent is extended or adjusted under 35 U.S.C. 154(b) by 666 days.

(21) Appl. No.: 12/447,889

(22) PCT Filed: Nov. 9, 2007

(86) PCT No.: PCT/AU2007/001719
§ 371 (c)(1),
(2), (4) Date: Jan. 19, 2010

(87) PCT Pub. No.: WO2008/055310
PCT Pub. Date: May 15, 2008

(65) Prior Publication Data
US 2010/0136172 A1    Jun. 3, 2010

(30) Foreign Application Priority Data
Nov. 10, 2006 (AU) .................. 2006906288

(51) Int. Cl.
*C12H 1/04* (2006.01)
*A23C 9/12* (2006.01)

(52) U.S. Cl.
USPC .................................. 426/271; 426/63

(58) Field of Classification Search
USPC .................................. 426/271
See application file for complete search history.

(56) References Cited

U.S. PATENT DOCUMENTS

| 5,171,845 | A | 12/1992 | Spik et al. |
| 5,596,082 | A * | 1/1997 | Kussendrager et al. ...... 530/416 |
| 6,010,698 | A * | 1/2000 | Kussendrager et al. ...... 424/94.1 |
| 2005/0037955 | A1 | 2/2005 | Hooper et al. |
| 2008/0045456 | A1* | 2/2008 | Greenway et al. .............. 514/12 |
| 2009/0099128 | A1* | 4/2009 | Wu ................................. 514/54 |

FOREIGN PATENT DOCUMENTS

| EP | 0869134 B1 | 3/2002 |
| EP | 0704218 B1 | 3/2003 |
| EP | 0786473 B1 | 3/2005 |

(Continued)

OTHER PUBLICATIONS

Fedorova et al., "Milk Ultrafiltrate as a Promising Source of Angiogenin," *Applied Biochemistry and Microbiology*, vol. 38, No. 2, 2002, pp. 193-196.

Extended European Search Report for European Application No. 07815522, dated Apr. 4, 2011.

Rustam'yan et al. "Penetration of Cow Milk Angiogenin into the Blood of Mice After Peroral Introduction," *Biology Bulletin* 29:165-167 (2002).

(Continued)

*Primary Examiner* — Humera Sheikh
*Assistant Examiner* — Bhaskar Mukhopadhyay
(74) *Attorney, Agent, or Firm* — Clark & Elbing LLP

(57) ABSTRACT

The invention provides a process for the preparation of an angiogenin-enriched fraction from a milk product, the process comprising contacting the milk product with a cation exchange resin and eluting the angiogenin-enriched fraction from the cation exchange resin with a mobile phase. The invention also provides angiogenin-enriched fractions produced by process and food products, nutraceuticals and pharmaceutical comprising such angiogenin.

31 Claims, 2 Drawing Sheets

| Lane | sample |
|---|---|
| 1 | MW standards |
| 2 | |
| 3 | Angiogenin-enriched fraction |
| 4 | |
| 5 | |
| 6 | |
| 7 | |
| 8 | |
| 9 | |
| 10 | |

(56) References Cited

FOREIGN PATENT DOCUMENTS

| JP | 2003144095 | 5/2003 |
|---|---|---|
| JP | 2004331566 | 11/2004 |
| RU | 2110066 | 4/1998 |
| RU | 2204262 | 5/2003 |
| WO | WO 2004/106491 | 12/2004 |
| WO | WO 2006/054277 | 5/2006 |

OTHER PUBLICATIONS

Jang et al. "High Level Production of Bovine Angiogenin in *E. coli* by an Efficient Refolding Procedure" *Biotechnol Lett.* 26:1501-1504 (2004).

* cited by examiner

| Lane | sample |
|------|--------|
| 1 | MW standards |
| 2 | |
| 3 | Angiogenin-enriched fraction |
| 4 | |
| 5 | |
| 6 | |
| 7 | |
| 8 | |
| 9 | |
| 10 | |

PROCESS FOR THE PREPARATION OF ANGIOGENIN

CROSS REFERENCE TO RELATED APPLICATIONS

This application is the U.S. National Stage of International Application No. PCT/AU2007/001719, filed Nov. 9, 2007, which claims benefit of Australian patent application number 2006906288, filed Nov. 10, 2006, each of which is hereby incorporated by reference.

The present invention relates to a process for the preparation of an angiogenin-enriched fraction from a milk product, and to the use of such a fraction as a food additive, nutraceutical, or for the preparation of a therapeutic composition.

BACKGROUND

Angiogenin is a 14 kDa, non-glycosylated polypeptide which is produced by several growing cell types including vascular endothelial cells, aortic smooth muscle cells, fibroblasts, and some tumours such as colon carcinomas, ovarian carcinomas, and breast cancers. Angiogenin has been isolated from a number of sources including normal human plasma, bovine plasma, bovine milk, and mouse, rabbit and pig sera.

Angiogenin is homologous to pancreatic ribonuclease and has distinct ribonucleolytic activity. The protein is able to induce new blood vessel growth; however, it has not been established what role the ribonucleolytic activity of angiogenin plays in angiogenesis induced by this protein.

The concentration of angiogenin in normal human plasma is 60-120 ng/ml. However the concentration of the protein is elevated in patients affected by various types of cancer, and inhibition of angiogenin is known to prevent human tumour growth.

As well as a potent stimulator of angiogenesis, angiogenin has been shown to possess a number of other activities. These include the ability to remove skin defects such as pigmented spots, modulation of immune responses, protection of polymorphonuclear leukocytes from spontaneous degradation, and microbicidal activity against systemic bacterial and fungal pathogens. Based on the known physiological functions of the protein, various angiogenin applications in medicine, dietary foodstuff supplements and cosmetics can be predicted.

However the use of angiogenin in such applications requires an efficient process for the preparation of the protein on a commercial scale from an appropriate source. It is an aim of a preferred embodiment of the present invention to provide such a process. This process may also be included as part of an existing process for purification of other components of milk products, such as lactoferrin, lactoperoxidase or growth factors.

All references, including any patents or patent applications, cited in this specification are hereby incorporated by reference. It will be clearly understood that, although a number of prior art publications are referred to herein, this reference does not constitute an admission that any of these documents forms part of the common general knowledge in the art, in Australia or in any other country.

SUMMARY OF INVENTION

In a first aspect the invention provides a process for the preparation of an angiogenin-enriched fraction from a milk product, wherein said process comprises:

(a) contacting the milk product with a cation exchange resin;
(b) eluting an angiogenin-depleted lactoperoxidase fraction from the cation exchange column with a mobile phase of 0.30-0.38M (1.75-2.25% w/v) sodium chloride or equivalent ionic strength;
(c) eluting the angiogenin-enriched fraction from the Cation exchange resin with a mobile phase; and
(d) collecting the eluted angiogenin-enriched fraction, wherein the milk product is not subject to cation exchange chromatography prior to step (a) or after step (c).

The milk product may include whole milk, skim milk, buttermilk, whey, or colostrum. The amount of milk product contacted with the cation exchange resin is preferably about 16 column volumes (CV) to about 600 CV, more preferably about 16 CV to about 150 CV, and most preferably about 68 CV.

Preferably, the angiogenin-depleted lactoperoxidase fraction is eluted with a mobile phase containing 0.341 sodium chloride (2.0% w/v) or equivalent ionic strength, and which has a pH of 6.5.

In a further embodiment of the first aspect, it is preferred that prior to elution of the angiogenin-enriched fraction, the cation exchange resin is rinsed with a buffer of low ionic strength, (<0.34 M salt or its equivalent) or water, to remove milk product remaining in the column.

In a further embodiment of the first aspect, elution of the angiogenin-enriched fraction is with a mobile phase preferably containing 0.38-1.5M sodium chloride (2.25-8.7% w/v) or equivalent ionic strength, more preferably 0.38-0.59M sodium chloride (2.25-3.5% w/v) or equivalent ionic strength, and most preferably 0.43M chloride (2.5% w/v) or equivalent ionic strength.

In a further preferred embodiment, elution of the angiogenin-enriched fraction is with a mobile phase which has a pH in the range 4.0 to 9.0, preferably 5.5-7.5, and most preferably 6.5.

The cation exchange resin may comprise Sepharose beads. Preferably the Sepharose beads are in the size range 45-900 μm, and more preferably 90-300 μm.

In one embodiment, during step (a) of the process of the first aspect, the cation exchange resin is subject to a flow rate in the range of about 6-90 liters per liter resin per hour, more preferably about 6-50 liters per liter resin per hour, and most preferably about 33 liters per liter resin per hour.

The process according to the first aspect of the invention may be a continuous process or batch process. Preferably the process is a continuous process.

In one embodiment, the angiogenin-enriched fraction comprises an angiogenin content of at least 2% w/w, preferably at least 10% w/w, more preferably at least 20% w/w.

In a further embodiment, the angiogenin-enriched fraction is further treated to reduce the amount of non-angiogenin proteins and/or salt present in the composition.

In a second aspect the invention provides an angiogenin-enriched fraction, when prepared by a process according to the first aspect of the invention.

In a third aspect the invention provides the use of an angiogenin-enriched fraction according to the second aspect of the invention, in the preparation of a food substance or nutraceutical. In a preferred embodiment, the food substance is a sport nutrition or an infant food supplement.

In a fourth aspect the invention provides a food substance or nutraceutical comprising an angiogenin-enriched fraction according to the second aspect of the invention.

In a fifth aspect the invention provides a pharmaceutical composition comprising an angiogenin-enriched fraction according to the second aspect of the invention, and a pharmaceutically acceptable carrier.

In a sixth aspect the invention provides the use of an angiogenin-enriched fraction according to the second aspect of the invention, in the preparation of a medicament for the treatment or prophylaxis of diseases caused by viruses, bacteria, or fungi and their toxins, or diseases where the stimulation of angiogenesis is required.

In a seventh aspect the invention provides the use of an angiogenin-enriched fraction according to the second aspect of the invention, as an ingredient for a nutraceutical which can target pathogens which cause infections of human mucosal surfaces. In a preferred embodiment, the mucosal surfaces may include those of the nose, eyes, ears, lungs, breast and vagina.

In an eighth aspect the invention provides a method of targeting pathogens which cause infections of human mucosal surfaces, comprising the step of administering an effective amount of a nutraceutical according to a fourth aspect of the invention, or a composition according to a fifth aspect of the invention, to a subject.

In a ninth aspect the invention provides a method of treating diseases, including those caused by viruses, bacteria, or fungi and their toxins, comprising the step of administering an effective amount of a nutraceutical according to a fourth aspect of the invention, or a composition according to a fifth aspect of the invention, to a subject.

DETAILED DESCRIPTION

Figure 1:
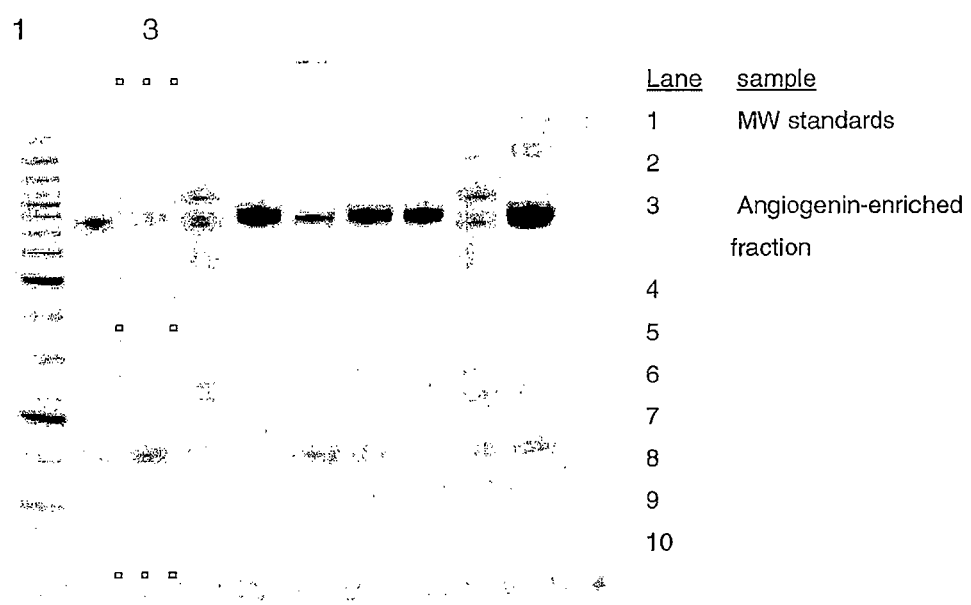
FIG. 1 is an SDS-polyacrylamide gel electrophoresis of an eluted angiogenin-enriched fraction prepared by the process of the invention.

The inventors have recognised the need for a process which allows the preparation of an angiogenin-enriched fraction in an efficient manner. Accordingly, the first aspect of the invention provides such a process wherein a milk product is contacted with a cation exchange column, and an angiogenin-enriched fraction is eluted therefrom with a mobile phase.

The term "angiogenin-enriched" is taken to mean that the angiogenin protein:total protein ratio present in the eluted fraction is increased relative to the ratio present in the milk product before cation exchange chromatography. For the fraction to be considered angiogenin-enriched, it should have an angiogenin content of at least 2% w/w, preferably at least 10% w/w, and more preferably at least 20% w/w.

As used herein, the term "fraction" refers to a partially purified portion of the milk product.

Use of the term "efficient" is taken to mean an inexpensive and quick process when compared to methods which are currently employed to enrich for proteins, including angiogenin.

A suitable milk product may include whole milk, skim milk, buttermilk, whey (such as acid or cheese/renneted whey) or a whey derivative (such as whey protein concentrate or whey protein isolate flow through), and colostrum. The milk product is not subject to cation exchange chromatography prior to the process of the present invention.

It will be apparent to those skilled in the art that the milk product may be obtained from any lactating animal, e.g. ruminants such as cows, sheep, buffalos, goats, and deer, non-ruminants including primates such as a human, and monogastrics such as pigs. It is preferred that skim milk which is derived from whole cow's milk is used in the process of the present invention.

The process according to the first aspect of the invention uses only one cation exchange resin or column. Various types of cation exchange resin matrices may be used, and would be known in the art. These include for example any support based on cross-linked polysaccharide, e.g. cross-linked agarose (Sepharose) or dextran (Sephadex), any support based on cellulose, e.g. fibres and beads (Sephacel, Gibco HB), granules (Gibco HG), or styrene-divinylbenzene copolymer (Dowex resin), or any support based on polyacrylamide, e.g. hydroxylated methacrylic polymer (Tosoh HW).

The appropriate resin functional groups will also be known to the person skilled in the art and include sulphopropyl (SP), carboxymethyl (CM), orthophosphate/phosphoric acid, e.g. Whatman P11, methyl sulfonate (S), carboxylic acid, and sulphonic acid (50 W).

It is preferred that the resin which is chosen will have a minimum bead diameter of 45 µm and a maximum diameter of 900 µm. Optimally, the bead diameter will be between 90 µm and 300 µm.

In a preferred embodiment, SP Sepharose cation exchange resin beads which have a bead diameter in the range 45-165 µm and in the range 100-300 µm are suitable for angiogenin adsorption and purification.

The resin is typically packed in a 10 cm deep column; however the depth of the column may vary from 4 cm to 200 cm depending on the amount of angiogenin which is desired to be obtained. The column diameter will also vary depending on the application. Typically the diameter is in the range of 0.9 cm to 200 cm, and optimally the diameter is 62 cm. The column which houses the resin may be constructed from any suitable material including stainless steel, plastic, or glass.

The flow rate at which the milk product is adsorbed to the cation exchange column during the contact step may be varied depending on the scale of the process and the type of milk product used. The lower limit of the flow rate is determined by cost-effectiveness for an industrial-type application, whereby at very low flow rates the cost to run the process exceeds the return.

In a preferred embodiment, the milk product is skim milk, and the milk is applied to the column at a rate of 6-90 liters per liter of resin per hour (h) (linear flow 60-900 cm per h). Preferably the flow rates used are in the range of 6-50 liters per liter of resin per hour (linear flow 60-500 cm per h), and more preferably 34 liters per liter of resin per hour (linear flow 331 cm per h). High flow rates are suitable for angiogenin purification provided the total amount of milk product contacted with the resin is limited. Using the above-mentioned flow rates it has been found that for optimum fractionation of angiogenin, the amount of skim milk for example which is in contact with the cation exchange resin is in the range of about 16-600 column (bed) volumes, preferably 16-150 column volumes, and more preferably 68 column volumes.

Whilst milk product volumes greatly exceeding the resin volume are suitable for preparation of other milk products such as lactoperoxidase and lactoferrin, as described in Australian Patent no. 613688, the present inventors have found that a milk product volume to resin volume in the order of 1000 column volumes (liters milk product per liter resin) is unsuitable for angiogenin preparation by the process of the invention. The inventors have found that milk product volume to resin volume in excess of about 600 column volumes results in little angiogenin binding to the resin, and the angiogenin recovered will not be enriched relative to the starting material. Therefore the preferred upper limit according to the invention, in the case of skim milk, is about 600 column volumes, preferably about 150 column volumes, and most preferably about 68 column volumes. As the milk product to resin ratio increases the amount of angiogenin bound, and the purity of the eluted angiogenin, gradually decreases. As for the flow rate, the lower limit is set by commercial concerns rather than column-related factors. If the volume of milk product loaded declines much below 16 column volumes, a point is reached where the rinse and elution times exceed the point where sufficient angiogenin can be purified to make the process economically viable.

In contacting the milk product with the cation exchange resin to allow the angiogenin to adsorb, the pH of the source is preferably about 6.5, although it is not necessary to adjust the pH for the process of the present invention.

In eluting the angiogenin which is adsorbed to the column, a mobile phase consisting of a buffer solution having an ionic strength of 0.38-1.5M is used. The type of salt used in the mobile phase is not limited and would be known to the person skilled in the art. For example any soluble, non-toxic buffer can be used such as the soluble sodium, potassium, calcium, magnesium or lithium salts of chloride, citrate, phosphate, acetate, sulphate, bicarbonate, hydroxide, imidazole, or maleate. Synthetic zwitterion buffers such as Trizma, HEPES or tricine may also be used.

As the ionic strength increases above 0.6M, the purity of the angiogenin decreases as non-angiogenin proteins begin to elute, thus diluting the angiogenin with other proteins. In a preferred embodiment, the mobile phase consists of sodium chloride at an ionic strength of 0.38-1.5M (2.25-8.7% w/v), and more preferably at an ionic strength of 0.38-0.59M (2.25-3.5% w/v). Most preferably, an ionic strength equivalent to 0.43M sodium chloride (2.5%) or less is used.

The mobile phase may have a pH within a broad range, such as 4.0-9.0, preferably 5.5-7.5, and most preferably about 6.5. At the upper and lower limits both protein stability and the ability of proteins to bind to the cation exchange resin become influenced. A pH in the range 5.5-7.5 provides the highest angiogenin purity without lowering yields.

The volume and flow rate of the mobile phase may also vary. For example a mobile phase consisting of 1-20 liters of buffer solution per liter of resin may be used. Preferably the range is from 1-10 liters, and more preferably 2.5 liters of buffer solution per liter of resin is used. The mobile phase preferably flows at a rate between 6-90 liters per liter of resin per hour (60-900 cm/h). More preferably the rate is between 6-40 (60-400 cm/h), and most preferably the optimal linear flow rate is 7.5 liters per liter of resin per hour (75 cm/h).

The process according to the first aspect of the invention may be performed in isolation to prepare an angiogenin-enriched fraction, or may be incorporated as part of an integrated fractionation process in which other desired milk product components are fractionated. For example prior to the elution of the angiogenin-enriched fraction from the cation exchange column, an angiogenin-depleted lactoperoxidase fraction may be eluted from the column. The type of buffer used for elution of the lactoperoxidase fraction, as well as the buffer flow rate and volume is typically identical to that which may be used for elution of the angiogenin fraction, as described above. However the ionic strength of the buffer will be different. For example the buffer consists of sodium chloride at an ionic strength of 0.3-0.38M (1.75-2.25% w/v), and preferably the lactoperoxidase elution buffer has an ionic strength equivalent to 0.34M sodium chloride (2.0%).

Furthermore, once the lactoperoxidase and angiogenin fractions have been eluted, a lactoferrin fraction may be eluted from the column. Again the type of buffer used for elution of the lactoferrin fraction, as well as the buffer flow rate and volume is typically identical to that which may be used for elution of the lactoperoxidase and angiogenin fractions, as described above. However the ionic strength of the buffer will be different. For example the buffer may consist of sodium chloride at an ionic strength of 0.59-3.0M (3.5-17.4% w/v), more preferably at an ionic strength of 0.68-2.0M (4.0-11.7% w/v), and most preferably the lactoferrin elution buffer has an ionic strength equivalent to 1.5M sodium chloride (8.75%).

In a further embodiment of the first aspect of the invention, following the step of loading the cation exchange column with the milk product, any unbound protein within the cation exchange column may be removed by rinsing the column with a buffer of low ionic strength, or with water. If a buffer is used, the ionic strength of the buffer will typically be less than 0.34M, and is preferably less than 0.05M. Suitable buffers, their pH, and volumes are identical to those described above for the elution of the lactoperoxidase, angiogenin, and lactoferrin fractions.

However the rinse buffer flow rate is preferably 15 liters per liter of resin per hour (147 cm/h).

The angiogenin-enriched fraction prepared by the process of the present invention may be further treated to remove non-angiogenin proteins and/or to remove salt. This may be considered important for the production of standardised food substances or nutraceuticals, and for the preparation of therapeutics. Such steps may be achieved by membrane filtration, ideally ultrafiltration, or equivalent as would be known in the art, e.g. dialysis, electrodialysis, size-exclusion chromatography, solid-phase extraction, nanofiltration or other known means. The angiogenin-rich retentate is retained, and the permeate is discarded.

If ultrafiltration is chosen, membrane sizes are preferably in the range of 0.15-10 kDa NMWCO, and most preferably 5 kDa NMWCO.

Since angiogenin is involved in a number of physiological functions, the preparation of this protein using the process according to the invention provides an ideal and economical source of the protein which can subsequently be directed towards these functions. For example the purified protein may be used in the preparation of a food substance or nutraceutical. A typical food substance includes sports nutrition powder, which increases athletic performance following consumption, or an infant food supplement.

The term "nutraceutical" as used herein refers to an edible product isolated or purified from food, in this case from a milk product, which is demonstrated to have a physiological benefit or to provide protection or attenuation of an acute or chronic disease or injury when orally administered. The nutraceutical may thus be presented in the form of a dietary preparation or supplement, either alone or admixed with edible foods or drinks. The nutraceutical may have positive clinical effects on cardiovascular disease, Crohn's disease or conditions involving non-healing wounds, for example ulcers.

The nutraceutical composition may be in the form of a soluble powder, a liquid or a ready-to-drink formulation. Alternatively, the nutritional composition may be in solid form; for example in the form of a ready-to-eat bar or breakfast cereal. Various flavours, fibres, sweeteners, and other additives may also be present.

The nutraceutical preferably has acceptable sensory properties (such as acceptable smell, taste and palatability), and may further comprise vitamins and/or minerals selected from at least one of vitamins A, B1, B2, B3, B5, B6, B11, B12, biotin, C, D, E, H and K and calcium, magnesium, potassium, zinc and iron.

The composition may be fed to a subject via a nasogastric tube, jejunum tube, or by having the subject drink or eat it.

The nutraceutical composition may be produced as is conventional; for example, the composition may be prepared by blending together the protein and other additives. If used, an emulsifier may be included in the blend. Additional vitamins and minerals may be added at this point but are usually added later to avoid thermal degradation.

If it is desired to produce a powdered nutraceutical composition, the protein may be admixed with additional components in powdered form. The powder should have a moisture content of less than about 5% by weight. Water, preferably water which has been subjected to reverse osmosis, may then be mixed in to form a liquid mixture.

If the nutraceutical composition is to be provided in a ready to consume liquid form, it may be heated in order to reduce the bacterial load. If it is desired to produce a liquid nutraceutical composition, the liquid mixture is preferably aseptically filled into suitable containers. Aseptic filling of the containers may be carried out using techniques commonly available in the art. Suitable apparatus for carrying out aseptic filling of this nature is commercially available.

The angiogenin-enriched fraction prepared by the process of the present invention may also be formulated in a pharmaceutical composition suitable for administration to a subject.

Preferably the composition also comprises one or more pharmaceutically acceptable carriers, diluents or excipients. Such compositions may comprise buffers such as neutral buffered saline, phosphate buffered saline and the like; carbohydrates such as glucose, mannose, sucrose or dextrans; mannitol; proteins; polypeptides or amino acids such as glycine; antioxidants; chelating agents such as EDTA; adjuvants and preservatives. Compositions of the present invention may be formulated for intravenous administration, topical application or oral consumption.

Such a composition may be administered to a subject in a manner appropriate to the disease to be treated and/or prevented. The quantity and frequency of administration will be determined by such factors as the condition of the subject and the type and/or severity of the subject's disease. Appropriate dosages may also be determined by clinical trials. An effective amount of the composition can be determined by a physician with consideration of individual differences in age, weight, disease severity, condition of the subject, route of administration and any other factors relevant to treatment of the subject. Essentially, an "effective amount" of the composition is an amount which is sufficient to achieve a desired therapeutic effect.

In another aspect, the present invention provides methods for the treatment and/or prevention of diseases. Such treatment methods comprise administering to a subject an effective amount of a nutraceutical or pharmaceutical composition as described above. Preferably such diseases include those caused by viruses, bacteria, or fungi and their toxins. However since angiogenin plays a role in angiogenesis, diseases where the stimulation of angiogenesis is required may also be treated using an angiogenin-containing composition of the invention. These diseases include coronary artery disease, stroke, ischaemic limb disease, and delayed wound healing.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It must also be noted that, as used in the subject specification, the singular forms "a", "an" and "the" include plural aspects unless the context clearly dictates otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention is now further described in detail by reference to the following example. The example is provided for purposes of illustration only, and is not intended to be limiting unless otherwise specified. Thus, the invention encompasses any and all variations which become evident as a result of the teaching provided herein.

Example 1

Process for the Preparation of an Angiogenin-Enriched Fraction from Skim Milk

A 10 cm deep column was packed with SP Sepharose Big Beads (GE Healthcare) such that the total bed volume of the column was 29.7 liters. To the column a flow of skimmed cow's milk was applied at a linear flow rate of 331 cm/h (34 liters of skimmed milk per liter of resin per hour) for 2 hours until the volume of skimmed milk applied was 68 times the volume of the resin packed into the column.

The milk remaining in the column was removed by adding 2.5 column volumes (CV) of water at a linear flow rate of 147 cm/h (15 liters of buffer per liter of resin per hour), or 0.25 CV/min, for 10 min.

The angiogenin-depleted lactoperoxidase fraction was eluted from the column with 2.5 CV of a buffer containing sodium ions equivalent to 2.0% (0.34M) NaCl, at pH 6.5, by flowing the cation buffer solution at a linear flow rate of 75 cm/h (7.5 liters of cation buffer solution per liter of resin per hour), or 0.125 CV/min, for 20 min. The first 0.5 liters of cation buffer solution per liter of resin was discarded to drain and the next 2.5 liters of cation buffer solution per liter of resin was collected as the angiogenin-depleted lactoperoxidase fraction (including 0.5 liters of cation buffer solution per liter of resin overlapping the application time of the next buffer, i.e. breakthrough time).

The angiogenin-enriched fraction was then eluted from the column with 2.5 CV of a buffer containing sodium ions equivalent to 2.5% w/v (0.43 M) NaCl, at pH 6.5, by flowing the cation buffer solution at a linear flow rate of 75 cm/h (7.5 liters of cation buffer solution per liter of resin per hour), or 0.125 CV/min, for 20 min. The first 0.5 liters of cation buffer solution per liter of resin was discarded to drain and the next 2.5 liters of cation buffer solution per liter of resin was collected as the angiogenin-enriched fraction (including 0.5 liters of cation buffer solution per liter of resin overlapping the application time of the next buffer).

Finally, the lactoferrin fraction is eluted from the column with 2.5 CV of a buffer containing sodium ions equivalent to 8.75% w/v (1.5 M) NaCl, at pH 6.5, by flowing the cation buffer solution at a linear flow rate of 75 cm/h (7.5 liters of cation buffer solution per liter of resin per hour), or 0.125 CV/min, for 20 min. The first 0.5 liters of cation buffer solution per liter of resin was discarded to drain and the next 2.5 liters of cation buffer solution per liter of resin was collected as the lactoferrin fraction.

The angiogenin-enriched fraction that was collected was ultrafiltrated (NMWCO 5 kDa) to concentrate and reduce the salt content. The resultant concentrate was freeze-dried and stored at room temperature for subsequent use.

Figure 2:
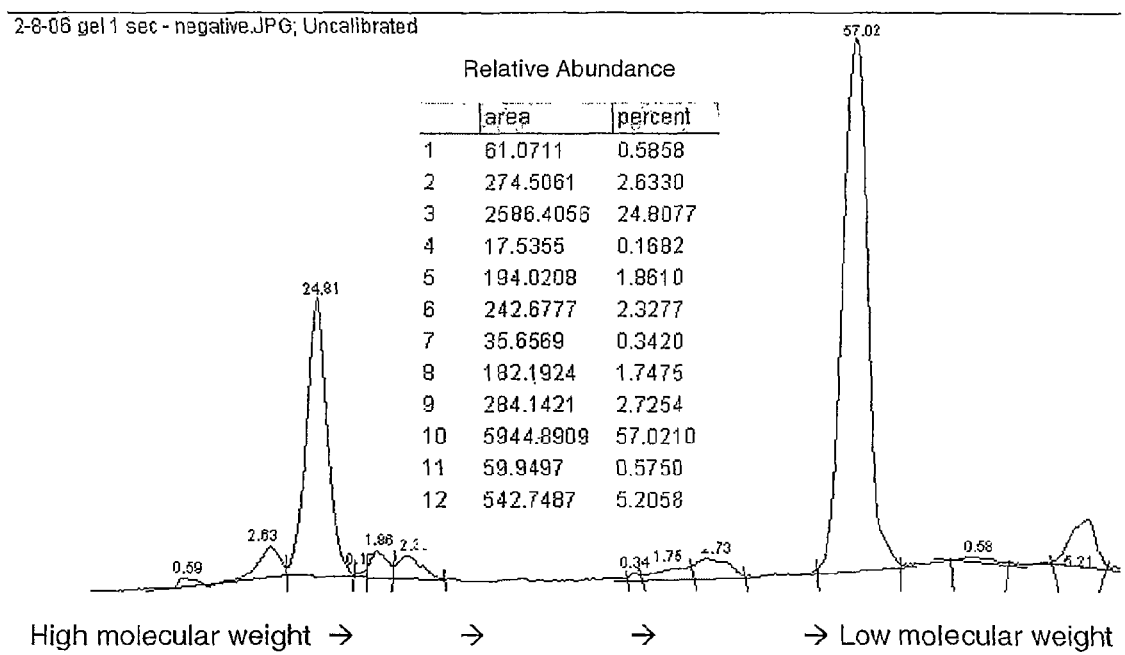
FIG. 2 shows the results of a gel densitometer analysis of the SDS-PAGE separation of the angiogenin-enriched fraction (FIG. 1).

The angiogenin-enriched fraction was analysed for angiogenin content by SDS-PAGE (FIG. 1), and the fraction was found to contain 57% (protein basis) of a low molecular weight (14 kDa) protein (FIG. 2) which was confirmed to be angiogenin by MALDI-TOF/TOF MS (results not shown).

It would be clear to a person skilled in the art that this angiogenin preparation process can be scaled up for commercial purposes.

The claims defining the invention are as follows:

1. A process for the preparation of an angiogenin-enriched fraction from a milk product, wherein the process uses only one cation exchange chromatography step, wherein said process comprises comprising: (a) contacting the milk product with a cation exchange resin; (b) eluting an angiogenin-depleted lactoperoxidase fraction from the cation exchange column with a mobile phase of 0.30-0.38M (1.75-2.25% w/v) sodium chloride or equivalent ionic strength; (c) eluting the angiogenin-enriched fraction from the cation exchange resin with a mobile phase; and (d) collecting the eluted angiogenin-enriched fraction, wherein the milk product is not subject to cation exchange chromatography prior to step (a) or after step (c) and wherein said angiogenin-enriched fraction comprises an angiogenin content of at least 20% w/w compared to total protein in said fraction.

2. The process according to claim 1, wherein the milk product is selected from the group consisting of whole milk, skim milk or buttermilk.

3. The process according to claim 1, wherein the amount of milk product contacted with the cation exchange resin is about 16 column volumes to about 600 column volumes.

4. The process according to claim 1, wherein the amount of milk product contacted with the cation exchange resin is about 16 column volumes to about 150 column volumes.

5. The process according to claim 1, wherein the amount of milk product contacted with the cation exchange resin is about 68 column volumes.

6. The process according to claim 1, wherein elution of the angiogenin-depleted lactoperoxidase fraction is with a mobile phase containing 0.34M sodium chloride (2.0% w/v) or equivalent ionic strength, and which has a pH of 6.5.

7. The process according to claim 1, wherein prior to elution of the angiogenin-enriched fraction, the cation exchange resin is rinsed with a buffer of low ionic strength, (<0.34 M salt or its equivalent) or water, to remove milk product remaining in the column.

8. The process according claim 1, wherein elution of the angiogenin-enriched fraction is with a mobile phase containing 0.38-1.5M sodium chloride (2.25-3.5% w/v) or equivalent ionic strength.

9. The process according to claim 1, wherein elution of the angiogenin-enriched fraction is with a mobile phase containing 0.38-0.59M sodium chloride (2.25-3.5% w/v) or equivalent ionic strength.

10. The process according to claim 1, wherein elution of the angiogenin enriched fraction is with a mobile phase containing 0.43M sodium chloride (2.5% w/v) or equivalent ionic strength.

11. The process according to claim 1, wherein elution of the angiogenin-enriched fraction is with a mobile phase which has a pH in the range 4.0-9.0.

12. The process according to claim 1, wherein elution of the angiogenin-enriched fraction is with a mobile phase which has a pH in the range 5.5-7.5.

13. The process according to claim 1, wherein elution of the angiogenin-enriched fraction is with a mobile phase which has a pH of 6.5.

14. The process according to claim 1, wherein the cation exchange resin comprises cross-linked agarose beads.

15. The process according to claim 14, wherein the cross-linked agarose beads are in the size range 45-900 um.

16. The process according to claim 14, wherein the cross-linked agarose beads are in the size range 90-300 Urn.

17. The process according to claim 1, wherein during step (a), the cation exchange resin is subject to a flow rate in the range of about 6-90 liters per liter resin per hour.

18. The process according to claim 17, wherein the contact flow rate is in the range of about 6-50 liters per liter resin per hour.

19. The process according to claim 17, wherein the contact flow rate is in the range of about 33 liters per liter resin per hour.

20. The process according to claim 1, wherein the process is a continuous process or a batch process.

21. The process according to claim 1, wherein the angiogenin-enriched fraction comprises an angiogenin content of at least 2% w/w.

22. The process according to claim 1, wherein the angiogenin-enriched fraction is further treated to reduce the amount of non-angiogenin proteins and/or salt present in the composition.

23. A food substance or nutraceutical comprising an angiogenin-enriched fraction prepared by the process according to claim 1.

24. The food substance or nutraceutical of claim 23, wherein the food substance is a sport nutrition or infant food supplement.

25. A pharmaceutical composition comprising an angiogenin enriched fraction prepared by the process according to claim 1, and a pharmaceutically acceptable carrier.

26. A method of treating diseases caused by viruses, bacteria, or fungi and their toxins, or diseases where the stimulation of angiogenesis is required, wherein said method comprises administering an angiogenin-enriched fraction prepared by the process according to claim 1.

27. A method of treating pathogens which cause infections of human mucosal surfaces, said method comprising administering a nutraceutical comprising an angiogenin-enriched fraction prepared by the process according to claim 1.

28. A method of targeting pathogens which cause infections of human mucosal surfaces, comprising the step of administering the composition according to claim 25 to a subject.

29. A method of treating diseases caused by viruses, bacteria, or fungi and their toxins, or diseases where the stimulation of angiogenesis is required, comprising the step of administering the composition according to claim 25 to a subject.

30. The method according to claim 27, wherein the mucosal surfaces are selected from the group consisting of the nose, eyes, ears, lungs, breast and vagina.

31. The method according to claim 28, wherein the mucosal surfaces are selected from the group consisting of the nose, eyes, ears, lungs, breast and vagina.

* * * * *

UNITED STATES PATENT AND TRADEMARK OFFICE
CERTIFICATE OF CORRECTION

| | | |
|---|---|---|
| PATENT NO. | : 8,551,547 B2 | Page 1 of 1 |
| APPLICATION NO. | : 12/447889 | |
| DATED | : October 8, 2013 | |
| INVENTOR(S) | : Andrew Brown et al. | |

It is certified that error appears in the above-identified patent and that said Letters Patent is hereby corrected as shown below:

In the Claims

Column 9, Line 16, Claim 1, delete "wherein".

Line 17, Claim 1, delete "comprises".

Column 10, Line 10, Claim 15, replace "um" with --µm--.

Line 12, Claim 16, replace "Um" with --µm--.

Signed and Sealed this
Second Day of December, 2014

Michelle K. Lee
*Deputy Director of the United States Patent and Trademark Office*